(12) United States Patent  
Wieters et al.

(10) Patent No.: US 8,206,288 B2  
(45) Date of Patent: Jun. 26, 2012

(54) ENDOSCOPE WITH RESISTANCE HEATER

(75) Inventors: Martin Wieters, Hamburg (DE); Andreas Mückner, Schwarzenbek (DE)

(73) Assignee: Olympus Winter & IBE GmbH, Hamburg (DE)

( * ) Notice: Subject to any disclaimer, the term of this patent is extended or adjusted under 35 U.S.C. 154(b) by 595 days.

(21) Appl. No.: 12/498,673

(22) Filed: Jul. 7, 2009

(65) Prior Publication Data

US 2010/0016671 A1 Jan. 21, 2010

(30) Foreign Application Priority Data

Jul. 8, 2008 (DE) .......................... 10 2008 031 924

(51) Int. Cl.
*A61B 1/00* (2006.01)
(52) U.S. Cl. ........................................ 600/169; 600/129
(58) Field of Classification Search .................. 600/129, 600/169
See application file for complete search history.

(56) References Cited

U.S. PATENT DOCUMENTS

| 4,076,018 A | | 2/1978 | Heckele |
| 4,724,303 A | * | 2/1988 | Martin et al. .................. 219/216 |
| 5,533,496 A | * | 7/1996 | De Faria-Correa et al. .. 128/898 |
| 5,605,532 A | * | 2/1997 | Schermerhorn .............. 600/169 |
| 5,647,840 A | * | 7/1997 | D'Amelio et al. ............ 600/169 |
| 5,845,634 A | | 12/1998 | Parker |
| 6,065,934 A | * | 5/2000 | Jacot et al. .................... 416/155 |
| 6,248,060 B1 | * | 6/2001 | Buess et al. .................. 600/182 |
| 7,938,774 B2 | * | 5/2011 | Segawa .......................... 600/169 |
| 2007/0149856 A1 | * | 6/2007 | Segawa .......................... 600/169 |
| 2010/0010313 A1 | * | 1/2010 | Muckner et al. ............. 600/169 |

FOREIGN PATENT DOCUMENTS

JP 2006-000282 A 1/2006

* cited by examiner

*Primary Examiner* — John P Leubecker
(74) *Attorney, Agent, or Firm* — Scully, Scott, Murphy & Presser, P.C.

(57) ABSTRACT

A medical endoscope and insertion portion for a medical endoscope having a fiber tube that encloses an image guide and is surrounded by optical fibers, the distal opening of said fiber tube being sealed by a window, which is heated by an electric resistance heater located close by, wherein the heater is designed as heating foil arranged on the outer surface of the fiber tube.

10 Claims, 1 Drawing Sheet

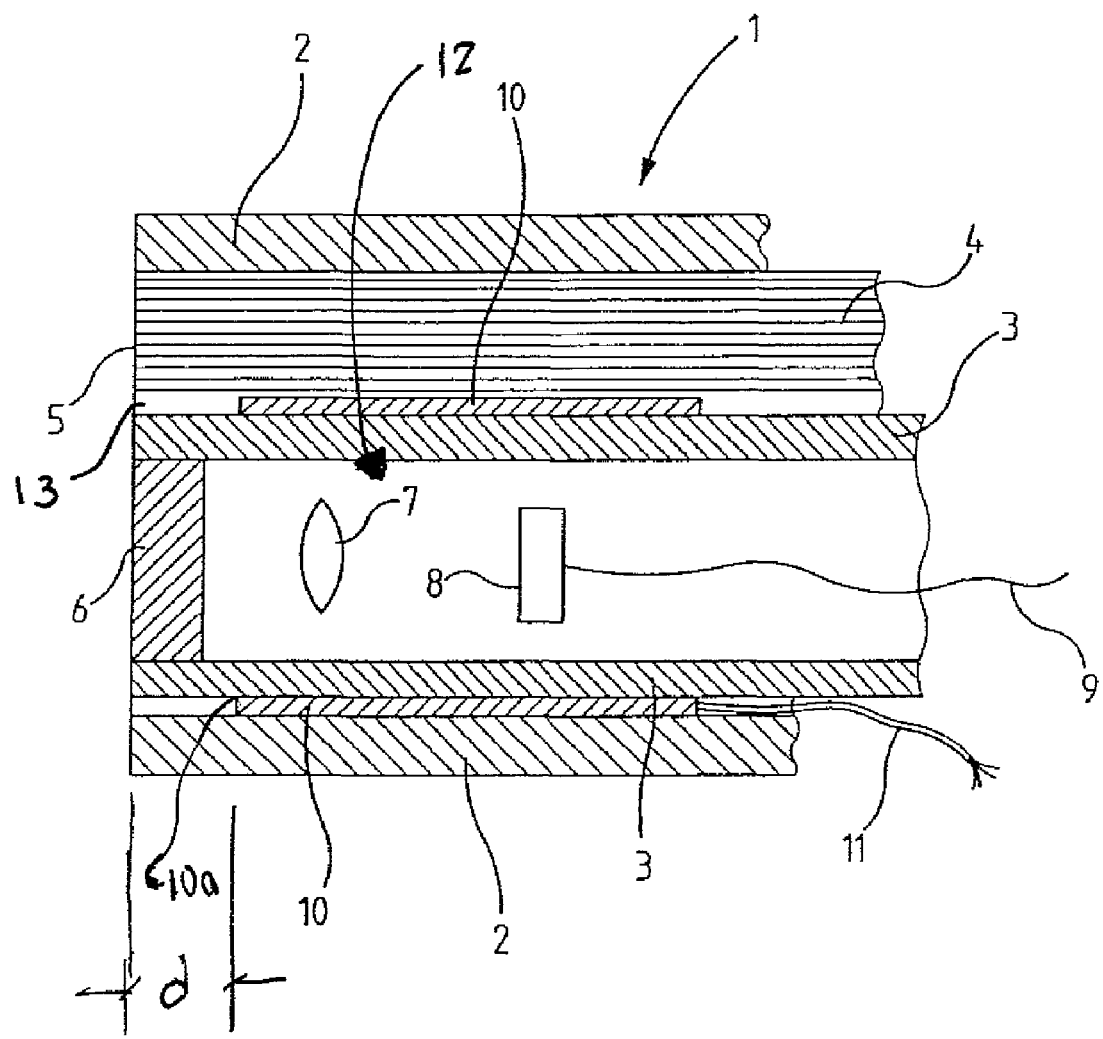

ENDOSCOPE WITH RESISTANCE HEATER

BACKGROUND

1. Field of the Invention

The present invention relates generally to medical endoscopes and, more particularly, to an endoscope having a resistance heater.

2. Prior Art

Medical endoscopes are used for insertion in damp and warm body cavities, while they themselves retain the cooler room temperature. This results in the endoscope becoming misted, which is particularly annoying in the case of a window provided on the endoscope, because the misting impedes visibility through the window.

It has therefore been known for some time, to heat the window in order to prevent misting. Apart from other heating methods, such as those using light, hot gas or hot liquid, generally electric resistance is mainly used, which is located close to the window in the endoscope.

For example, U.S. Pat. No. 4,076,018 shows an endoscope having a window looking out to the side, against which is positioned a heating conductor. U.S. Pat. No. 4,076,018 also mentions other possibilities, such as a heating coating on the window.

US 2007/0149856 A1 shows an endoscope, where a heating ring is positioned in the area between the window and a system tube, which accommodates the optical system and is located within the fiber tube. US 2007/0149856 A1 also shows a temperature control sensor located adjacent to the window.

JP 2006000282 shows an endoscope, where a heating coil is arranged around the edge of the window.

The known designs fulfill their purpose of keeping the window mist-free, but have design disadvantages. The arrangement of the heating device close to the window makes the design of the endoscope, which is in any case very constricted, even worse. It is also particularly difficult to ensure adequate thermal contact between the heater and window.

SUMMARY

According to the present invention, the heating of the window is developed as a heating foil, which is arranged on the outer surface of the fiber tube. The heating foil can be developed in large area contact with the fiber tube, which can comprise metal and ensures good thermal transport through the fiber tube to the window, which can be soldered to the fiber tube to achieve good thermal contact. The arrangement on the outer surface of the fiber tube produces the advantage that the inside of the fiber tube is not made complicated as a result of the heating. It is also possible in the case of a conventional endoscope design, to retrofit a heating foil to the fiber tube with ready fitted internal fittings. Heating foils also have the advantage that they are available cheaply in any size. They can be easily fitted because of their flexibility. The heating foil can be located at a distance from the front face of the endoscope. It can be potted, together with the optical fibers, with suitable plastic material at the distal end section of the endoscope and is therefore well protected against contact and particularly against moisture.

BRIEF DESCRIPTION OF THE DRAWINGS

These and other features, aspects, and advantages of the apparatus and methods of the present invention will become better understood with regard to the following description, appended claims, and accompanying drawings where:

The FIGURE diagrammatically illustrates an axial section through a distal end section of an endoscope.

DETAILED DESCRIPTION OF THE PREFERRED EMBODIMENT

The FIGURE shows a distal end of an insertion portion of a medical endoscope 1 with an outer tube 2 that eccentrically encloses a fiber tube 3, at a distance. The fiber tube 3 is so named because it is typically surrounded by optical fibers for guiding illumination light to illuminate the area of operation. Thus, the space between the outer tube 2 and the fiber tube 3 is typically filled with optical fibers 4, which end distally in the front face 5 of the endoscope 1. The distal opening of the fiber tube 3 is sealed by a window 6, which is vapor-tight, for example, is soldered around the edge with the fiber tube 3 consisting of metal. Inside the fiber tube 3 is an image guide 12 comprising a lens 7 and a video camera 8, which transports the images to the outside via a cable 9 which runs proximally inside the fiber tube 3.

In another embodiment, other image guides may also be provided, such as a relay lens array or an image guide bundle. The camera 8 looks through the lens 7 and the window 6 towards the outside. The optical parts within the fiber tube 3 are kept dry by the latter's hermetic seal. On the outside of the window 6, misting does, however, occur. In order to prevent this misting, a heater is provided for the window 6, in the form of a heating foil 10 and is wound around an outer surface of the fiber tube 3.

The distal edge 10a of the foil 10, as shown in the FIGURE, is arranged offset at a distance d from the front face 5. The area from the front face 5 to the distal edge 10a of the foil 10 is potted together with the optical fibers 4 using a potting material 13 and is therefore well sealed. The heating foil 10 is connected to the outside by a cable 11, which can contain four conductors as shown in the FIGURE. Two of the conductors can be used to connect a heat resistor in the foil 10, which can be arranged as a heating layer or meandering resistance sheet, for example. Two further conductors can be used to connect a temperature sensor located on the foil, with which the temperature of the window 6 can be controlled, in order to enable more rapid heating.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A medical endoscope comprising:
   an outer tube;
   an image guide;
   a fiber tube that encloses the image guide;
   optical fibers disposed within the outer tube and outside of the fiber tube;
   a window disposed at a distal opening of the fiber tube; and
   an electric resistance heater for heating the window, wherein the electric resistance heater is a heating foil arranged proximate to the window on an outer surface of the fiber tube.

2. The endoscope according to claim 1, wherein a distal edge of the heating foil is located offset from a front face of the endoscope.

3. The endoscope according to claim 2, wherein a space between the front face of the endoscope and the distal edge of the heating foil is filled with a potting material.

4. The endoscope according to claim 1, wherein the fiber tube is metallic.

5. The endoscope according to claim 4, wherein a distal portion of the fiber tube contacts the window so as to conduct heat from the heating foil to the window via the fiber tube.

6. An insertion portion for a medical endoscope, the insertion portion comprising:
   an outer tube;
   an image guide;
   a fiber tube that encloses the image guide;
   optical fibers disposed within the outer tube and outside of the fiber tube;
   a window disposed at a distal opening of the fiber tube; and
   an electric resistance heater for heating the window, wherein the electric resistance heater is a heating foil arranged proximate to the window on an outer surface of the fiber tube.

7. The insertion portion according to claim 6, wherein a distal edge of the heating foil is located offset from a front face of the endoscope.

8. The insertion portion according to claim 7, wherein a space between the front face of the endoscope and the distal edge of the heating foil is filled with a potting material.

9. The insertion portion according to claim 6, wherein the fiber tube is metallic.

10. The insertion portion according to claim 9, wherein a distal portion of the fiber tube contacts the window so as to conduct heat from the heating foil to the window via the fiber tube.

* * * * *